United States Patent
Wittorff et al.

(10) Patent No.: US 11,351,162 B2
(45) Date of Patent: *Jun. 7, 2022

(54) ORAL DELIVERY VEHICLE CONTAINING FLAVORING AGENTS

(71) Applicant: FERTIN PHARMA A/S, Vejle (DK)

(72) Inventors: Helle Wittorff, Vejle Øst (DK); Heidi Ziegler Bruun, Vejle Øst (DK); Dorthe Schackinger Boesen, Vejle (DK)

(73) Assignee: FERTIN PHARMA A/S, Vejle (DK)

( * ) Notice: Subject to any disclaimer, the term of this patent is extended or adjusted under 35 U.S.C. 154(b) by 76 days.

This patent is subject to a terminal disclaimer.

(21) Appl. No.: 16/682,169

(22) Filed: Nov. 13, 2019

(65) Prior Publication Data

US 2020/0078349 A1    Mar. 12, 2020

Related U.S. Application Data

(63) Continuation of application No. 15/356,175, filed on Nov. 18, 2016, now Pat. No. 10,543,205.

(51) Int. Cl.
*A61K 9/20*    (2006.01)
*A61K 31/465*    (2006.01)

(52) U.S. Cl.
CPC .......... *A61K 31/465* (2013.01); *A61K 9/2018* (2013.01); *A61K 9/2086* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 4,627,977 A | 12/1986 | Gaffar et al. | |
| 4,820,506 A | 4/1989 | Kleinberg et al. | |
| 5,576,014 A | 11/1996 | Mizumoto et al. | |
| 5,874,068 A | 2/1999 | Engelman et al. | |
| 6,024,981 A | 2/2000 | Khankari et al. | |
| 6,146,661 A | 11/2000 | Hoshino | |
| 7,067,149 B1 | 6/2006 | Chauveau et al. | |
| 8,435,542 B2 | 5/2013 | Manley et al. | |
| 8,658,139 B1 | 2/2014 | Cutler | |
| 2003/0022912 A1 | 1/2003 | Martino et al. | |
| 2009/0311320 A1 | 12/2009 | Oury et al. | |
| 2011/0123462 A1 | 5/2011 | Mordas et al. | |
| 2011/0250247 A1 | 10/2011 | Boghmans et al. | |
| 2013/0302387 A1 | 11/2013 | Pedersen | |
| 2014/0328973 A1* | 11/2014 | Nielsen .............. | A23G 4/08 426/2 |
| 2015/0101627 A1 | 4/2015 | Marshall et al. | |
| 2016/0120793 A1 | 5/2016 | Abdalla et al. | |
| 2016/0145203 A1 | 5/2016 | Gambogi et al. | |
| 2018/0140521 A1 | 5/2018 | Geonnotti et al. | |

FOREIGN PATENT DOCUMENTS

| | | | |
|---|---|---|---|
| CN | 1709229 A | 12/2005 | |
| EP | 0413427 A2 | 2/1991 | |
| EP | 0497439 A1 | 8/1992 | |
| EP | 0913148 A1 | 6/1999 | |
| EP | 0922464 A1 * | 6/1999 | ........... A61K 9/2018 |
| EP | 0922464 A1 | 6/1999 | |
| EP | 1369109 A1 | 12/2003 | |
| GB | 1526020 | 9/1978 | |
| WO | 9932092 A1 | 7/1999 | |
| WO | 02102357 A1 | 12/2002 | |
| WO | 2006063189 A2 | 6/2006 | |
| WO | 2009007768 A1 | 1/2009 | |
| WO | 2009080023 A1 | 7/2009 | |
| WO | 2010104563 A2 | 9/2010 | |
| WO | 2013125350 A1 | 8/2013 | |
| WO | 2016061486 A1 | 4/2016 | |
| WO | 2018091048 A1 | 5/2018 | |
| WO | 2018091050 A1 | 5/2018 | |

OTHER PUBLICATIONS

Roquette (Signet Chemical Corp., Products, SWEETPEARL, available at http://www.signetchem.com/product.aspx?prdid=1044, accessed on May 13, 2019).*
Bolhuis GK Rexwinkel EG Zuurman K: "Polyols as filler-binders for disintegrating tablets prepared by direct compaction", Drug Development and Industrial Pharmacy, New York, NY, US, vol. 35, No. 6, Jun. 2009 (Jun. 2009), pp. 671-677, XP008162413, ISSN: 0363-9045, DOI: 10.1080/03639040802587799 the whole document.
Module. (1992) In C.G.Morris (Ed ), Academic Press Dictionary of Science and Technology. (4th ed.) [Online] Oxford: Elsevier Science & Technology. Available at http://search.credoreference.com/content/entry/apdst/rnodule/0.
Patent Cooperation Treaty: International Search Report and Written Opinion of PCT/DK2019/050152; Gimenez Miralles, J.; dated Aug. 22, 2019; 11 pages.
Patent Cooperation Treaty: International Search Report and Written Opinion of PCT/DK2019/050153; Hartinger, Stefan; dated Sep. 30, 2019; 18 pages.
Patent Cooperation Treaty: International Search Report and Written Opinion of PCT/DK2019/050154; Gimenez Miralles, J.; dated Sep. 20, 2019; 12 pages.

(Continued)

*Primary Examiner* — H. Sarah Park
(74) *Attorney, Agent, or Firm* — Gregory M. Howison

(57) ABSTRACT

The invention relates an oral delivery vehicle tablet containing nicotine, the delivery vehicle tablet being formed by compression of a plurality of particles, the oral delivery vehicle tablet comprising nicotine, the oral delivery vehicle tablet comprising sugar alcohol(s) in an amount of 40 to 100% by weight of the delivery vehicle tablet, wherein at least 10% by weight of the delivery vehicle tablet comprises a plurality of particles consisting of erythritol and wherein the delivery vehicle tablet comprises a plurality of further sugar alcohol particles in an amount of at least 10% by weight of the delivery vehicle tablet, wherein said further sugar alcohol particles comprise at least one sugar alcohol and wherein said further sugar alcohols particles have a composition which is different from said particles consisting of erythritol.

15 Claims, No Drawings

(56) References Cited

OTHER PUBLICATIONS

Patent Cooperation Treaty: International Search Report and Written Opinion of PCT/DK2019/050155; Nyeki, Agnes; dated Sep. 11, 2019; 12 pages.
Patent Cooperation Treaty: International Search Report and Written Opinion of PCT/DK2019/050156; Hartinger, Stefan; dated Sep. 20, 2019; 17 pages.
Patent Cooperation Treaty: International Search Report and Written Opinion of PCT/DK2019/050157; Nyeki, Agnes; dated Sep. 16, 2019; 11 pages.
Patent Cooperation Treaty: International Search Report and Written Opinion of PCT/DK2019/050158; Gimenez Miralles, J.; dated Aug. 8, 2019; 11 pages.
Patent Cooperation Treaty: International Search Report and Written Opinion of PCT/DK2019/050159; Nyeki, Agnes; dated Aug. 22, 2019; 11 pages.
Patent Cooperation Treaty: International Search Report and Written Opinion of PCT/DK2019/050160; Hartinger Stefan; dated Sep. 20, 2019; 17 pages.
Patent Cooperation Treaty: PCT Application No. PCT/DK2017/050342: International Search Report; 6 pages; dated Nov. 30, 2017; Ceyte, Mathilde.
Patent Cooperation Treaty: PCT Application No. PCT/DK2017/050342: Written Opinion; 8 pages; dated Nov. 30, 2017; Ceyte, Mathilde.
Patent Cooperation Treaty: PTC Application No. PCT/DK2016/050377: International Search Report and Written Opinion; 12 pages; dated Aug. 3, 2017; Ceyte, Mathilde.
Roquette Product page of Sweet Pearl Maltitol USP/NF, EP, , 1 page.
Stefan W. Wessel et al.: "Potential benefits of chewing gum for the delivery of oral therapeutics and its possible role in oral healthcare", Expert Opinion on Drug Delivery, vol. 13, No. 10, Jun. 3, 2016 (Jun. 3, 2016), pp. 1421-1431, XP055609672, GB ISSN: 1742-5247, DOI: 10.1080/17425247.2016.1193154 p. 1422; table 1.
Pharmaburst 500 ODT (available at https://www.americanpharmaceuticalreview.com/25260-excipients/6023668-Pharmaburst-500/, accessed on May 7, 2021).

* cited by examiner

ORAL DELIVERY VEHICLE CONTAINING FLAVORING AGENTS

CROSS-REFERENCE TO RELATED APPLICATIONS

This application is a continuation of U.S. patent application Ser. No. 15/356,175, filed Nov. 18, 2016, entitled ORAL DELIVERY VEHICLE CONTAINING NICOTINE, the contents of which are incorporated by reference herein in their entirety.

TECHNICAL FIELD

The invention relates to an oral delivery vehicle containing nicotine.

BACKGROUND

In the prior art it is well-known to provide oral delivery vehicles containing nicotine made by compression and where a substantial part of the delivery vehicle is comprised of a sugar alcohol. It is also well-known that such delivery vehicles may be very attractive for delivery of active ingredients orally. Such substances may include pharmaceuticals, nutrients, flavors, vitamins, smoke inhibitors, dietary supplements, etc.

A challenge related to such delivery vehicles is that the user of such vehicles, e.g. tablets, is more and more focused on convenience and attractive taste. Such requirements do very often conflict with what is technically possible. This is in particular relevant to delivery vehicles in the form of tablets of compressed particles.

It is an object of the invention to provide an oral delivery vehicle suitable for delivery of such active ingredients in oral cavity of a user, and it is an object to obtain a delivery vehicle which may deliver such active ingredients in the oral cavity of a user in such a way that the user finds the delivery process attractive.

SUMMARY

The invention relates to an oral delivery vehicle tablet containing nicotine, the delivery vehicle tablet being formed by compression of a plurality of particles, the oral delivery vehicle tablet containing nicotine, the oral delivery vehicle tablet comprising sugar alcohol(s) in an amount of 40 to 100% by weight of the delivery vehicle tablet, wherein at least 10% by weight of the delivery vehicle tablet comprises a plurality of particles consisting of erythritol and wherein the delivery vehicle tablet comprises a plurality of further sugar alcohol particles in an amount of at least 10% by weight of the delivery vehicle tablet, wherein said further sugar alcohol particles comprise at least one sugar alcohol and wherein said further sugar alcohols particles have a composition which is different from said particles consisting of erythritol.

The invention also relates to an oral delivery vehicle tablet without nicotine in all the embodiments of the delivery vehicle tablet containing nicotine, the delivery vehicle tablet being formed by compression of a plurality of particles, the oral delivery vehicle tablet comprising sugar alcohol(s) in an amount of 40 to 100% by weight of the delivery vehicle tablet, wherein at least 10% by weight of the delivery vehicle tablet comprises a plurality of particles consisting of erythritol and wherein the delivery vehicle tablet comprises a plurality of further sugar alcohol particles in an amount of at least 10% by weight of the delivery vehicle tablet, wherein said further sugar alcohol particles comprise at least one sugar alcohol and wherein said further sugar alcohols particles have a composition which is different from said particles consisting of erythritol.

In the present context, the particles consisting of erythritol are referred to as particles which has not been preprocessed by granulation with other sugar alcohols or binders for the purpose of obtaining so-called direct compressible particles (DC).

The present invention benefits from a synergy between the particles consisting of erythritol and the further sugar alcohol particles. The further sugar alcohols may be e.g. sorbitol which is direct compressible by nature or it may be other sugar alcohols which have been preprocessed, e.g. by granulation with a suitable binder. At the same time the particles consisting of erythritol serves as a means for salivation which is both attractive to the user and also serves for the purpose of dissolving the further sugar alcohol particles when the tablet is chewed as fast as possible.

The use of particles consisting of erythritol, i.e. non-DC grade erythritol, was not expected to work by the inventors of the present invention since the general expectation in the art of tablet pressing is that only DC grade erythritol would be possible to use in a tablet.

Suitable sugar alcohols typically constitute from about 40 to about 100% by weight of the tablet, such as about 80 to about 99% by weight of the tablet.

When including gum base in the formulation sugar alcohols typically constitute from about 5 to about 95% by weight of the tablet, more typically about 20 to about 80% by weight such as 30 to 70% or 30 to 60% by weight of the tablet.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the chewing gum formulation.

A tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

In an embodiment of the invention the particles consisting of erythritol are non-DC grade particles, where non-DC stands for particles which are not directly compressible in a tableting process.

According to a further embodiment of the invention, the applied particles consisting of erythritol is best characterized as being not-directly compressible (non-DC). The use of non-DC erythritol when compared to conventionally applied direct compressible erythritol (DC) has shown remarkable effects to the users perception of the delivery vehicle when chewed. This may partly be due to the somewhat larger size of non-DC erythritol, when compared to DC-erythritol, but is may also be a result of a high content of erythritol in the individual particles applied for compression. DC-erythritol, which for obvious reasons are marketed and applied for compression purposes, does not result in such improved salivation effect and taste.

It should be noted that the terminology non-DC is easily understood within the field of technology. Suppliers or sugar alcohol provides clear guidance to the user as for the ability for use in relation to compression of tablets. A non-DC particle in this connection is referred to as a particle which is not expressly recommended by the supplier for compression. Example of a non-DC grade of erythritol is Zerose™ erythritol 16952F supplied by Cargill whereas an example of a direct compressible (DC) grade of erythritol include Zerose™ DC 16966 also supplied by Cargill.

In an embodiment of the invention the particles consisting of erythritol are defined as non-DC grade with reference to the Compressibility Index according to European Pharmacopeia 6.0 and where particles consisting of erythritol are having a compressibility index which is greater than 21%.

In an embodiment of the invention the particles consisting of erythritol are defined as non-DC with reference to the Compressibility Index according to European Pharmacopeia 6.0 and where particles consisting of erythritol are having a compressibility index which is greater than 21% and less than 37%.

In an embodiment of the invention the further sugar alcohol particles are directly compressible (DC).

The terminology directly compressible is well-known within the art of tableting, i.e. in technical field of compression of particles in a gathered compressed tablet. Directly compressible is routinely referred to as DC by many manufactures of such particles.

In an embodiment of the invention the further sugar alcohol particles are defined as DC with reference to the Compressibility Index according to European Pharmacopeia 6.0 and where said further sugar alcohol particles are having a compressibility index which is less than 21%, such as less than 15%, such as less than 10%.

In an embodiment of the invention the further sugar alcohol particles includes particles comprising sugar alcohols selected from the group of sorbitol, erythritol, xylitol, lactitol, maltitol, mannitol or isomalt or any combination thereof.

An example of such DC grade of sugar alcohol includes ISOMALT DC 101 provided by Züdsucker.

A further example of a DC grade sugar alcohol includes Zerose™ DC 16966 supplied by Cargill. It is here noted that the understanding of direct compressible is simply designated by DC. Unless otherwise stated, this terminology will be applied throughout the present application.

In an embodiment of the invention friability of the delivery vehicle tablet is less than 2%, such as less than 1.5%, wherein friability is measured according to European Pharmacopoeia 9.1, test method 2.9.7, by using a pharmaceutical friability-tester PTF 10E from Pharma Test.

According to an embodiment of the invention is has been showed that a desired friability may in fact be obtained even with a stable tablet and an attractive mouthfeel and taste. The desired mouthfeel is still obtained even in spite of the fact that binders, such as the further sugar alcohols, would typically compromise this mouthfeel and taste in a compressed tablet and in spite of the fact that the use of the particles consisting of erythritol should compromise the friability when used on such amount.

In an embodiment of the invention friability of the delivery vehicle tablet is greater than 0.2%, wherein friability is measured according to European Pharmacopoeia 9.1, test method 2.9.7, by using a pharmaceutical friability-tester PTF 10E from Pharma Test.

In an embodiment of the invention said particles consisting of erythritol and said further sugar alcohol particles are of different composition, wherein said particles consisting of erythritol have an average particle size which is larger than the average particle size of said further sugar alcohol particles, wherein the average particle size is determined according to European Pharmacopoeia 9.1 when using test method 2.9.38 particle size distribution estimation by analytical sieving.

The composition of minimum two different types of sugar alcohol particles, the first sugar alcohol particles and the second sugar alcohol particles, may be different by having different chemical nature, different hygroscopicity, different solubility, different particle size, different flowability and/or different morphology may provide the user with a unique sensory experience In an embodiment of the invention the particle size of at least 80% of the particles consisting of erythritol is greater than 200 micron, such as greater than 225 micron, such as greater than 250 micron and wherein the particle size is determined according to European Pharmacopoeia 9.1 when using test method 2.9.38 particle size distribution estimation by analytical sieving.

According to this embodiment, it has been realized that the size of the particles consisting of erythritol features an improved salivation and mouthfeel combined with a feasible breaking force of the tablet.

In an embodiment of the invention the particle size of less than 20% of the particles consisting of erythritol is smaller than 250 micron, such as less than 15% of the particles consisting of erythritol is smaller than 250 micron, such as less than 10% of the particles consisting of erythritol is smaller than 250 micron and wherein the particle size is determined according to European Pharmacopoeia 9.1 when using test method 2.9.38 particle size distribution estimation by analytical sieving.

In an embodiment of the invention the tablet comprises more than 10% by weight of compressed particles consisting of erythritol wherein the resistance to crunching of the tablet is greater than 60N, such as greater than 70N, such as greater than 80N, such as greater than 90N, such as greater than 100 N, such as greater than 110, such as greater than 130N such as greater than 150N, wherein the resistance to crunching of the tablet is less than 300N, such as less than 250N, such as less than 200N, wherein the resistance to crunching is determined according to European Pharmacopoeia 9.1, test method 2.9.8, by using a pharmaceutical resistance to crunching tester model Pharma Test type PTB 311.

In an embodiment of the invention the delivery vehicle tablet comprises at least one module, wherein the module comprises more than 10% by weight of compressed particles consisting of erythritol wherein the resistance to crunching of the module is greater than 60N, such as greater than 70N, such as greater than 80N, such as greater than 90N such as greater than 100 N, wherein the resistance to crunching is determined according to European Pharmacopoeia 9.1, test method 2.9.8, by using a pharmaceutical resistance to crunching tester model Pharma Test type PTB 311.

The module may typically be gathered from a plurality of compressed particles and have a weight which is greater than 0.2 gram and less than 10.

In an embodiment of the invention a module is defined as a plurality of particles being compressed together to form a gathered module of particles.

In an embodiment of the invention the delivery vehicle tablet comprises a plurality of delivery vehicle tablet modules.

In an embodiment of the invention the plurality of modules are slice-like layers.

In an embodiment of the invention the delivery vehicle tablet comprises at least two modules, wherein the delivery vehicle tablet comprises more than 10% by weight of compressed particles consisting of erythritol wherein the resistance to crunching of a first module comprising of compressed particles consisting of erythritol is less than 150N, wherein the resistance to crunching of a second module is more than 100N and more than the resistance to crunching of the first module, wherein the second module comprises less compressed particles consisting of erythritol with respect to weight than the first module, wherein the resistance to crunching of the delivery vehicle tablet is higher than the resistance to crunching of the second module when the second module is separated from the tablet, wherein the resistance to crunching is determined according to European Pharmacopoeia 9.1, test method 2.9.8, by using a pharmaceutical resistance to crunching tester model Pharma Test type PTB 311.

According to a further embodiment of the invention, the delivery vehicle may be in the form of a multi-module delivery vehicle. This multi-module may have the benefit that the overall hardness of the compressed delivery vehicle may be improved by the application of a module which by itself has a higher hardness than the module comprising the substantial amount of non-DC erythritol. Non-DC erythritol may have the effect that the module in which large amount of the non-Dc erythritol features a relatively low hardness. This may under certain circumstances be not desirable due to the fact that such low hardness may reflect a relatively low cohesiveness of the vehicle, thereby resulting in an increased friability of the vehicle. Under some circumstances this relatively low hardness may on the other hand reflect that the non-DC is present in substantial amounts and the low hardness may also make the non-DC easily and fast available in particular for the purposes of the second action. When applying a further module having high hardness such as a module formed by substantial amounts of compressed sugar alcohols such as sorbitol, xylitol, isomalt, etc, this support module may both delivery hardness and when broken into pieces during the initial chew benefit from the salivation effect obtained through the non-DC erythritol of the supported module. The third action, i.e. dissolving of sugar alcohols in not only obtained in the non-DC erythritol module but it is also obtained in relation to the sugar alcohols of the support module featuring less salivation effect.

In an embodiment of the invention the oral delivery vehicle tablet comprises 0-60 percent by weight of gum base, such as 10-60 percent by weight of gum base.

An advantage of the above embodiment may be that due to the relatively fast disintegration, the chewing together of the gum base by mastication in the oral cavity of obtained relatively fast.

In an embodiment of the invention the oral delivery vehicle tablet is free of gum base.

In an embodiment of the invention the oral delivery vehicle tablet comprises a pharmaceutically active ingredient.

According to an embodiment of the invention, the obtained taste and mouthfeel facilitates an attractive masking of otherwise not to well-tasting chemical substances. One such substance is nicotine, which when delivered through the mouth may cause a sensation referred to as burning. The present invention is advantageous for taste-masking purposes. The fast salivation and significant cooling may partly taste-mask even this badly-tasting substance. Such taste-masking may of course be obtained in relation to several other chemical substances.

In an embodiment of the invention the pharmaceutically active ingredient comprises nicotine.

In an embodiment of the invention the oral delivery vehicle tablet comprises an enhancer.

In an embodiment of the invention the enhancer comprises pH controlling agent, such as buffering agent.

In an embodiment of the invention the enhancer comprises a mucoadhesive agent.

In an embodiment of the invention the amount of binders is less than 10 percent by weight.

According to a further embodiment of the invention binders in separate particles may be used without compromising the advantageous taste and mouthfeel according to the invention. This is highly surprising as it appears that the presence if binders or other compression aiding substances appears to counteracts the desired effect, i.e. improved taste and mouthfeel.

In an embodiment of the invention the delivery vehicle tablet comprises flavor in an amount of 1-10% by weight of the delivery vehicle, such as 1-6% by weight of the delivery vehicle, such as 2-6% by weight of the delivery vehicle.

In embodiments of the present invention, the tablet comprises one or more flavoring agents selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, eucalyptus, mint, or any combination thereof.

In an embodiment of the invention the flavor is a powder flavor.

In an embodiment of the invention the flavor further includes a salivation agent.

The salivation agent may e.g. include Optaflow® supplied by Symrise AG. Such agent further encourages saliva production, thereby providing improved mouthfeel and supporting base and flavor performance.

In an embodiment of the invention the weight of particles consisting of erythritol contained in the oral delivery vehicle tablet is greater than 0.3 gram, such as greater than 0.4 gram, such as greater than 0.5 gram, such as greater than 0.6 gram, such as greater than 0.7 gram, such as greater than 0.8 gram, such as greater than 0.9 gram, such as greater than 1.0 gram.

According to a further embodiment of the invention, the amount of non-DC erythritol particles is relatively high. It is in particular high when considering that the erythritol in conventional sense is not regarded attractive for compression, but the mouthfeel and salivation perceived by the user is there improved significantly, when compared to low amounts or the same amounts of DC erythritol.

In an embodiment of the invention the weight of said particles consisting of erythritol contained in the oral delivery vehicle tablet is less than 3.0 gram, such as less than 2.0 gram, such as less than greater than 1.5 gram.

In an embodiment of the invention wherein the oral delivery vehicle tablet has a weight of between 0.5 and 4.0 grams.

In an embodiment of the invention wherein the weight ratio between said particles consisting of erythritol and said further sugar alcohol particles in the delivery vehicle tablet is greater than 0.3, such as greater than 0.4, such as greater than 0.5.

The weight ratio between particles consisting of erythritol and further sugar alcohol particles has proven significant according to an embodiment of the invention in the sense that a relatively high amount of particles consisting of erythritol must be present in order to obtain the mouthfeel and taste obtained through the invention. However, this taste and mouthfeel also resides in the so-called further sugar alcohol particles. An example of such sugar alcohol particle is xylitol, which, together with the particles consisting of erythritol may provide a mouthfeel which is unique and very attractive to test panels.

In an embodiment of the invention the weight ratio between said particles consisting of erythritol and said further sugar alcohol particles in the delivery vehicle tablet is greater than 0.3, such as greater than 0.4, such as greater than 0.5 and wherein said further sugar alcohol particles are DC sugar alcohol particles.

The weight ratio between particles consisting of erythritol and further sugar alcohol particles has proven significant as mentioned above in relation to the direct sensation and mouthfeel experienced by the user, but is has moreover addressed the challenge in relation to mouthfeel when DC sugar alcohol particles crumbles during the initial chew. The mechanical stability of the tablet is much desired when the tablet is in its non-chewed form, but a fast disintegration and dissolving is desirable when the tablet is chew due to the fact that user of the tablet dislike a sandy mouthfeel induced through small hard-pressed crumbles of DC sugar alcohol. The use of a very high amount of particles consisting of erythritol will facilitate a perceived fast dissolving and disintegration of the tablet after the initial chew.

In an embodiment of the invention the weight ratio between said particles consisting of erythritol and said further sugar alcohol particles in the delivery vehicle tablet is smaller than 0.7, such as smaller than 0.6, such as smaller than 0.55.

In an embodiment of the invention the weight ratio between said particles consisting of erythritol and said further sugar alcohol particles in the delivery vehicle tablet is smaller than 0.7, such as smaller than 0.6, such as smaller than 0.55 and wherein said further sugar alcohol particles are DC sugar alcohol particles.

The weight ratio between particles consisting of erythritol and further sugar alcohol particles is important for the purpose of obtaining an advantageous taste and mouthfeel. By having an upper limit of this ratio the chewer will moreover also experience a desirable crunch sensation when starting chewing the tablet, the crunch being obtained through the use of substantial amounts DC sugar alcohol particles.

According to an advantageous embodiment of the invention, the tablet may comprise filler.

In embodiments of the present invention, the tablet comprises filler in an amount of 0.1 to 50% by weight of the tablet, wherein the filler is hydrophobic and wherein at least 90% of the filler is contained in the tablet throughout the chewing of a user during a chewing period of at least 10 minutes.

In some embodiments of the invention, a buffer is added, the buffer being selected from the group consisting of a tris buffers, amino acid buffers, carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof.

When buffer is used, a preferred buffer is sodium bicarbonate and/or sodium carbonate. In some embodiments buffer is not part of the chewing gum formulation. In some other embodiments, buffer is part of the chewing gum formulation.

In some embodiments of the invention, the amount of buffer is 0.5 to 10% by weight of the tablet.

In some embodiments of the invention the buffer is selected from the group consisting of a carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, tris buffer, amino acids, and mixtures thereof.

In an embodiment of the invention the oral delivery vehicle tablet comprises said particles consisting of erythritol in an amount of 30 to 60% by weight of the tablet, said further sugar alcohol particles in an amount of 55 to 20% by weight of the tablet, wherein said further sugar alcohol particles comprises xylitol, Isomalt or sorbitol alone or in any combination thereof, and wherein said further sugar alcohol particles are directly compressible (DC), filler in an amount of 5 to 15% by weight of the tablet, and wherein the tablet comprises powdered flavor in an amount of 2 to 6% by weight of the tablet In an embodiment of the invention said further sugar alcohol comprises xylitol in an amount of more than 85% by weight of the further sugar alcohols.

In an embodiment of the invention the oral delivery tablet comprises two separate modules, wherein said modules are layers, wherein a first layer comprises said particles consisting of erythritol in an amount of 30 to 60% by weight of the modules and wherein said particles consisting of erythritol has a size which is larger than 250 micron, wherein the particle size is determined according to the European Pharmacopoeia 9.1 when using test method 2.9.38 particle size distribution estimation by analytical sieving, wherein a second layer comprises DC sugar alcohol particles in an amount of 80-100%, wherein the first layer has a resistance to crunching which is less than the resistance to crunching of the second layer and wherein the resistance to crunching is determined according to European Pharmacopoeia 9.1, test method 2.9.8, by using a pharmaceutical resistance to crunching tester model Pharma Test type PTB 311.

Moreover, the invention relates to a method of manufacturing an oral delivery vehicle according to any of the claims 1-39.

From the above it may be understood that it is possible to obtain a delivery vehicle, which, when applied as a chewing tablet may perform a fast disintegration in three different actions. The three actions are in principle not starting at the same time, and it should be understood that overlapping may occur due to the logic interaction between these actions.

The first action in this embodiment of the invention is where the user deposits the delivery vehicle in the mouth and chews the delivery vehicle. This chewing infers a mechanical crunching of the delivery vehicle. This has the consequence that the vehicle gradually, but still very fast, disintegrates into smaller distinct pieces of particles.

The second action, which is significant for obtaining the effect of this embodiment of the invention is that the non-DC erythritol has an attractive effect in the mouth of a user. It provides a cooling effect and a very attractive mouthfeel and taste for the user. Just as important is that the applied non-DC erythritol results in a significant salivation effect in the mouth of a user. This supplements the perceived mouthfeel of the user as this salivation effect is surprisingly convenient.

The third action is obtained as a result of the overall salivation effect. The salivation effect has the further benefit that smaller pieces of compressed particles of fast dissolvable sugar alcohols are dissolved faster due to the high amount of saliva. A fast dissolving of distinct particles in the mouth of the user is highly attractive to the user. Distinct particles in the mouth of a user in relation to chewing of a delivery vehicle is not perceived well by a user. It may, if the mouth feeling lasts too long result in a sandy/grain mouth feel.

According to an advantageous embodiment of the invention, the delivery vehicle may surprisingly be compressed as a one-module delivery vehicle, where the non-DC erythritol is mixed with other sugar alcohol(s) and optional other relevant substances such as pharmaceuticals, flavors, binders etc. It has thus been shown that a delivery vehicle featuring an acceptable hardness and at the same time the desired taste and mouthfeel when chewed may be obtained.

In an embodiment of the invention, the delivery vehicle tablet may moreover comprise flavors, dry-binders, tableting aids, anti-caking agents, emulsifiers, antioxidants, enhancers, absorption enhancers, buffers, high intensity sweeteners, softeners, colors, or any combination thereof.

DETAILED DESCRIPTION

In the following raw materials will refer to the mixed particles to be compressed into a tablet according to embodiments of the invention unless otherwise stated.

The following description outlines explanations of how the inventive oral delivery vehicle tablet may be produced and further details of what may be added to the inventive composition.

Typically, the process of manufacture of the inventive oral delivery vehicle tablet may be performed in a single tablet press, such as a rotary tablet press, for cost reasons. But it may be a benefit under some circumstances to apply a separate tablet press.

Preferably, the upper punch is convex which gives the upper face of the pressed tablet a concave form.

It should of course be noted that the shape of the punches may vary depending of the desired tablet shape.

In some embodiments of the invention, pressing said first tablet base material is performed at a force of 0.01 to 20 kN. Accordingly, the force may be relatively low in some embodiments. The benefit of a low force is to allow the powdered portion of the first tablet base material to form a sharp line at the interface of the die.

In some embodiments of the invention, wherein pressing said first tablet base material is performed at a force of 0.1 to 15 kN.

In some embodiments of the invention, wherein pressing said first tablet base material is performed at a force of 1 to 10 kN.

Important raw materials of the inventive tablet are particles consisting of erythritol and one or more further sugar alcohol particles. The further sugar alcohols particles are preferable sugar alcohols other than the particles consisting of erythritol.

In the present context, the particles consisting of erythritol are referred to as particles which have not been preprocessed by granulation with other sugar alcohols or binders for the purpose of obtaining so-called direct compressible particles.

The further sugar alcohol particles may typically refer to sugar alcohols known within the art as being direct compressible (DC).

According to a further embodiment of the invention, the applied particles consisting of erythritol is best characterized as being not-directly compressible (non-DC). The use of non-DC erythritol when compared to conventionally applied direct compressible erythritol (DC) has shown remarkable effects to the user's perception of the delivery vehicle when chewed. This may partly be due to the somewhat larger size of non-DC erythritol, when compared to DC-erythritol, but it may also be a result of a high content of erythritol in the individual particles applied for compression. DC-erythritol, which for obvious reasons are marketed and applied for compression purposes, does not result in such improved salivation effect and mouthfeel.

It should be noted that the terminology non-DC is easily understood within the field of technology. Suppliers or sugar alcohol provides clear guidance to the user as for the ability for use in relation to compression of tablets. A non-DC particle in this connection is referred to as a particle which is not expressly recommended by the supplier for compression. Example of a non-DC grade of erythritol is Zerose™ erythritol 16952F supplied by Cargill whereas an example of a direct compressible (DC) grade of erythritol include Zerose™ DC 16966 also supplied by Cargill.

Direct compressible sugar alcohols may include sorbitol which is DC by nature, DC grades of Xylitol, DC grades of Erythritol, DC grades of Mannitol, DC grades of maltitol, DC grades of Lactitol, Isomalt or other suitable DC grades of sugar alcohols.

The present invention benefits from a synergy between the particles consisting of erythritol and the further sugar alcohol particles. The further sugar alcohols may be e.g. sorbitol which is direct compressible by nature or it may be other sugar alcohols which has been preprocessed, e.g. by granulation with a suitable binder, to obtain particles which when compressed may encapsulate the particles consisting of erythritol into a mechanically stable tablet. At the same time the particles consisting of erythritol serves as a means for salivation which is both attractive to the user and also serves for the purpose of dissolving the further sugar alcohol particles when the tablet is chewed as fast as possible.

According to embodiments of the invention, encapsulated flavors or active ingredients may be added to the final blend of raw materials prior to compression.

Different methods of encapsulating flavors or active ingredients, which may both refer to flavors or active ingredients mixed into the raw materials to be compressed into the chewing gum may e.g. include spray drying, spray cooling, film coating, coascervation, Double emulsion method (Extrusion technology) or prilling.

Materials to be used for the above-mentioned encapsulation methods may e.g. include Gelatine, Wheat protein, Soya protein, Sodium caseinate, Caseine, Gum arabic, Mod. starch, Hydrolyzed starches (maltodextrines), Alginates, Pectin, Carregeenan, Xanthan gum, Locus bean gum, Chitosan, Bees wax, Candelilla wax, Carnauba wax, Hydrogenated vegetable oils, Zein and/or Sucrose.

Preferably, these ingredients should be added subsequent to any significant heating or mixing. In other words, the active ingredients should preferably be added immediately prior to the compression of the final tablet.

If applying the present invention in relation to chewing gum, the adding of active ingredients may be cautiously blended with pre-mixed gum base granulates and further ingredients such as the ingredients stipulated by the present claims, immediately prior to the final compression of the tablet.

In one embodiment the tablet according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and biguanidine (for instance chlorhexidine diacetate) and the following types of substances with limited water-solubility: quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171, 1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below mentioned compounds or derivates thereof but are not limited thereto: Acetaminophen, Acetylsalicylic acid, Buprenorphine, Bromhexin, Celcoxib, Codeine, Diphenhydramin, Diclofenac, Etoricoxib, Ibuprofen, Indometacin, Ketoprofen, Lumiracoxib, Morphine, Naproxen, Oxycodon, Parecoxib, Piroxicam, Pseudoefedrin, Rofecoxib, Tenoxicam, Tramadol, Valdecoxib, Calciumcarbonat, Magaldrate, Disulfiram, Bupropion, Nicotine, Azithromycin, Clarithromycin, Clotrimazole, Erythromycin, Tetracycline, Granisetron, Ondansetron, Prometazin, Tropisetron, Brompheniramine, Ceterizin, leco-Ceterizin, Chlorcyclizine, Chlorpheniramin, Chlorpheniramin, Difenhydramine, Doxylamine, Fenofenadin, Guaifenesin, Loratidin, des-Loratidin, Phenyltoloxamine, Promethazin, Pyridamine, Terfenadin, Troxerutin, Methyldopa, Methylphenidate, Benzalcon. Chloride, Benzeth. Chloride, Cetylpyrid. Chloride, Chlorhexidine, Ecabet-sodium, Haloperidol, Allopurinol, Colchinine, Theophylline, Propanolol, Prednisolone, Prednisone, Fluoride, Urea, Actot, Glibenclamide, Glipizide, Metformin, Miglitol, Repaglinide, Rosiglitazone, Apomorfin, Cialis, Sildenafil, Vardenafil, Diphenoxylate, Simethicone, Cimetidine, Famotidine, Ranitidine, Ratinidine, cetrizin, Loratadine, Aspirin, Benzocaine, Dextrometorphan, Phenylpropanolamine, Pseudoephedrine, Cisapride, Domperidone, Metoclopramide, Acyclovir, Dioctylsulfosucc., Phenolphtalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B, Chlorhexidine, Miconazole, Triamcinolonacetonid, Melatonine, Phenobarbitol, Caffeine, Benzodiazepiner, Hydroxyzine, Meprobamate, Phenothiazine, Buclizine, Brometazine, Cinnarizine, Cyclizine, Difenhydramine, Dimenhydrinate, Buflomedil, Amphetamine, Caffeine, Ephedrine, Orlistat, Phenylephedrine, Phenylpropanolamin, Pseudoephedrine, Sibutramin, Ketoconazole, Nitroglycerin, Nystatin, Progesterone, Testosterone, Vitamin B12, Vitamin C, Vitamin A, Vitamin D, Vitamin E, Pilocarpin, Aluminumaminoacetat, Cimetidine, Esomeprazole, Famotidine, Lansoprazole, Magnesiumoxide, Nizatide and or Ratinidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the tablet. The active agents, for which a controlled and/or accelerated rate of release is desired, are primarily substances with a limited water-solubility, typically below 10 g/100 ml inclusive of substances which are totally water-insoluble. Examples are medicines, dietary supplements, oral compositions, anti-smoking agents, highly potent sweeteners, pH adjusting agents, flavorings etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from ginkgo, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of compounds for the care or treatment of the oral cavity and the teeth are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, amino fluorides, stannous fluoride), phosphates, carbonates and selenium.

Cf. furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

In a further embodiment, the sucrose fatty acid esters may also be utilized for increased release of sweeteners including for instance the so-called highly potent sweeteners, such as for instance saccharin, cyclamate, aspartame, thaumatin, dihydrocalcones, stevioside, glycyrrhizin or salts or compounds thereof. For increased released of sweetener, the sucrose fatty acids preferable have a content of palmitate of at least 40% such as at least 50%.

Further Examples of Active Agents are Medicines of any Type.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocine-lactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., Nov. 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen®, Sildenafil citrate and derivatives thereof.

Dental products include Carbamide, CPP Caseine Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminum fluoride.

Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride, Vitamins include A, B1, B2, B6, B12, Folinic acid, Folic acid, niacin, Pantothenic acid, biotine, C, D, E, K. Minerals include Calcium, phosphor, magnesium, iron, Zinc, Cupper, Iod, Mangan, Crom, Selene, Molybden. Other active ingredients include: Q10®, enzymes. Natural drugs including Ginkgo Biloba, ginger, and fish oil.

The invention also relates to use of migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid. In a preferred embodiment the invention relates to the release of Nicotine and its salts.

In an embodiment of the invention, the powdered tablet materials beside the already described sugar alcohols selected from the group consisting of bulk sweeteners, flavors, dry-binders, tabletting aids, anti-caking agents, emulsifiers, antioxidants, enhancers, absorption enhancers, buffers, high intensity sweeteners, softeners, colors, or any combination thereof.

Suitable sugar alcohols typically constitute from about 40 to about 100% by weight of the tablet, such as about 80 to about 99% by weight of the tablet.

When including gum base in the formulation sugar alcohols typically constitute from about 5 to about 95% by weight of the tablet, more typically about 20 to about 80% by weight such as 30 to 70% or 30 to 60% by weight of the tablet.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the oral delivery vehicle formulation.

A tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phos¬phates, cellulose polymers and combinations thereof.

EXAMPLES

Examples 1-6. Preparation of Oral Delivery Vehicle Tablets Containing Nicotine

TABLE 1

Oral delivery vehicle compositions for 1.2 gram tablets containing nicotine. Amounts are given in wt-% of the tablet.

|  | Ex. 1 | Ex. 2 | Ex. 3 | Ex. 4 | Ex. 5 | Ex. 6 |
|---|---|---|---|---|---|---|
| Raw Material | T9 | T10 | T11 | T14 | T15 | T16 |
| Erythritol | 30 | 30 | 30 | 30 | 50 |  |
| Erythritol DC | — | — | — | — | — | 50 |
| Sorbitol | — | — | 56.15 |  |  |  |
| Xylitol DC | 55.03 | — | — | 23 |  |  |
| Isomalt DC | — | 56.15 | — | 31.15 | 36.12 | 36.12 |
| CaCO3 DC | 10 | 10 | 10 | 10 | 10 | 10 |
| Flavor | 4 | 3 | 3 | 5 | 3 | 3 |
| Ack | 0.1 | 0.1 | 0.1 | 0.1 | 0.1 | 0.1 |
| Sucralose | 0.02 | 0.25 | 0.25 | 0.25 | 0.25 | 0.25 |
| Glitter | 0.35 | — | — | — | 0.03 | 0.03 |
| Nicotine 16.5% | 0.5 | 0.5 | 0.5 | 0.5 | 0.5 | 0.5 |

The raw materials described above are generally well-known to the person skilled within the art. The nicotine is referring to nicotine polacrilex containing 16.5% by weight of nicotine. To avoid misunderstanding, it is also noted that Erythritol in the above and the following tables refers a non-DC grade of erythritol.

Process Flow

The compositions indicated in the above table 1 are processed into six corresponding tablets, as example 1-6.

For each examples 1-6 the raw materials are sieved with a 1600 micron sieve and then weighed into the proper amount according to the exampled compositions of table 1. It is noted that the final tablets of examples 1-6 are 1.2 gram tablets.

The weighed amounts are then added to a Turbula mixer in a stainless steel container and blended at 50 rpm for 5 minutes.

The mixtures are then tableted by means of a Manesty BB4 with two stations.

The applied molds have circular cross sections with diameters of 16 mm and are hollowed to produce tablets, which are concave and/or curved. Evidently, other mold size and shapes may be applied within the scope of the invention.

The resulting tablets according to Examples 1-6 are then obtained by tableting with a suitable pressure force. The applied tableting machine is not able to provide readings of pressure force, but the pressure force was chosen to fit the applied raw materials. In other words, the main determination of pressure force was related to the applied sugar alcohols, DC or non-DC.

Examples 7-12. Preparation of Flavor-Improved Oral Delivery Vehicle Tablets

TABLE 2

Oral delivery vehicle compositions for 1.2 gram tablets containing flavor. Amount are given in wt-% of the tablets.

|  | Ex. 7 | Ex. 8 | Ex. 9 | Ex. 10 | Ex. 11 | Ex. 12 |
|---|---|---|---|---|---|---|
| Raw Material | T9 | T10 | T11 | T14 | T15 | T16 |
| Erythritol | 30 | 30 | 30 | 30 | 50 |  |
| Erythritol DC | — | — | — | — | — | 50 |
| Sorbitol | — | — | 56.65 |  |  |  |
| Xylitol DC | 55.53 | — | — | 23 |  |  |
| Isomalt DC | — | 56.65 | — | 31.65 | 36.62 | 36.62 |
| CaCO3 DC | 10 | 10 | 10 | 10 | 10 | 10 |
| Flavor | 4 | 3 | 3 | 5 | 3 | 3 |
| Acesulfame-K | 0.1 | 0.1 | 0.1 | 0.1 | 0.1 | 0.1 |
| Sucralose | 0.02 | 0.25 | 0.25 | 0.25 | 0.25 | 0.25 |
| Glitter | 0.35 | — | — | — | 0.03 | 0.03 |
| Resistance to crunchiness | 70N | 110N | 141N | 106N | 90N | 138N |
| Friability | 2.5% | 0.82% | 0.56% | 2.0% | 2.2% | 0.55% |

Process Flow

The compositions indicated in the above table 2 are processed into six corresponding tablets, examples 7-12 according to the same process as explained with reference to examples 1-6. The main difference is that nicotine is not added to the composition of Table 2.

TABLE 2A

Evaluation of Examples 7-12.

| Example | Good - acceptable- poor | Suitability as chewable tablet | Watering effect 1-5, 1 low, 5 high |
|---|---|---|---|
| 7 | Acceptable | A loose structure, crumble | 4 |
| 8 | Acceptable | A bit hard but crunchy feeling | 3 |
| 9 | Poor | To hard structure | 2 |
| 10 | Acceptable | Crunchy fast dissolving feeling | 4 |
| 11 | Good | Nice crunchy chew | 5 |
| 12 | Poor | To hard structure | 4 |

The examples were evaluated according to two specific evaluation parameters, suitability as a chewable tablet and watering effect. It should be noted that the evaluation of the same parameters in relation to Examples 1-6 in essence gave the same result as the results indicated in Table 2A.

One interesting observation is that the example 11 has a very attractive mouthfeel as a chewing tablet. Another even more interesting observation is that both examples 8 and 10 has a better evaluation than example 12, even in spite of the fact that the amount of erythritol is higher in example 12.

Examples 13-20. Preparation of Two-Layer Flavor-Improved Oral Delivery Vehicle Tablets

TABLE 3

Oral delivery vehicle compositions for the first layer of bi-layer tablets containing flavor. Amount are given in wt-% of the tablet.

| | Ex. 13 | Ex. 14 | Ex. 15 | Ex. 16 | Ex. 17 | Ex. 18 | Ex. 19 | Ex. 20 |
|---|---|---|---|---|---|---|---|---|
| Raw Material | T1-L1 | T2-L1 | T3-L1 | T4-L1 | T5-L1 | T6-L1 | T7-L1 | T8-L1 |
| Erythritol | — | 20 | 30 | 50 | 50 | 50 | — | 20 |
| Erythritol DC | — | — | — | — | — | — | 50 | — |
| Sorbitol | 50 | 40 | — | 44.65 | — | — | — | — |
| Xylitol DC | 10 | — | — | — | 30 | 11 | — | — |
| Isomalt DC | — | — | 50 | — | | | 40 | — |
| CaCO3 DC | 36.62 | 36.65 | 16.65 | — | 16.62 | 35.62 | 6.65 | 6.62 |
| Maltitol DC | — | — | — | — | — | — | — | 70 |
| Flavor | 3 | 3 | 3 | 5 | 3 | 3 | 3 | 3 |
| Acesulfame-K | 0.1 | 0.1 | 0.1 | 0.1 | 0.1 | 0.1 | 0.1 | 0.1 |
| Sucralose | 0.25 | 0.25 | 0.25 | 0.25 | 0.25 | 0.25 | 0.25 | 0.25 |
| Color | 0.03 | — | — | — | 0.03 | 0.03 | — | 0.03 |

TABLE 4

Oral delivery vehicle compositions for the second layer of bi-layered tablets containing flavor. Amount are given in wt-% of the tablet.

| | Ex. 13 | Ex. 14 | Ex. 15 | Ex. 16 | Ex. 17 | Ex. 18 | Ex. 19 | Ex. 20 |
|---|---|---|---|---|---|---|---|---|
| Raw Material | T1-L2 | T2-L2 | T3-L2 | T4-L2 | T5-L2 | T6-L2 | T7-L2 | T8-L2 |
| Erythritol | — | 40 | 30 | 20 | 30 | — | — | 50 |
| Eryhtritol DC | 62 | — | — | — | — | — | 40 | — |
| Sorbitol | — | 48 | — | 65 | — | — | — | — |
| Xylitol DC | — | — | — | — | — | 61 | — | — |
| Isomalt DC | — | — | 55 | — | 50 | — | 40 | — |
| Maltitol DC | — | — | — | — | — | — | — | 30 |
| CaCO3 DC | 36.50 | 10.5 | 12.5 | 13.55 | 18.05 | 37.40 | 16.5 | 15.55 |
| Flavor | 1 | 1 | 2 | 1 | 1.5 | 1.2 | 3 | 4 |
| Acesulfame-K | 0.1 | 0.1 | 0.1 | — | — | — | 0.1 | — |
| Sucralose | 0.05 | 0.05 | 0.05 | 0.1 | 0.1 | 0.05 | 0.05 | 0.1 |
| Glitter | 0.35 | 0.35 | 0.35 | 0.35 | 0.35 | 0.35 | 0.35 | 0.35 |

Process Flow

The compositions indicated in the above tables 3 and 4 are processed into eight corresponding two-layer tablets with compositions as outlined in example 13-20.

For each examples 13-20 the raw materials are sieved with a 1600 micron sieve and then weighed into the proper amount according to the exampled compositions of table 1.

The weighed amounts are then added to a Turbula mixer in a stainless steel container and blended at 50 rpm for 5 minutes.

The mixtures are then tabletted by means of a Manesty BB4 with two stations.

The applied molds have circular cross sections with diameters of 16 mm and are hollowed to produce tablets, which are concave and/or curved. Evidently, other mold size and shapes may be applied within the scope of the invention.

The resulting tablets according to Examples 13-20 are then obtained by tableting with a suitable pressure force.

For each tablet of examples 13-20, a first layer as outlined in Table 3 in pressed initially at a first relatively low pressure. The blended composition of the second layer in then fed to the mold and a final two-layer tablet is then compressed at higher pressure than the pressure applied on the first layers, thereby producing final two-layer tablets according to Examples 13-20. It is noted that the final two-layer tablets of examples 13-20 are 1.8 gram tablets and that layer 1 of the tablets weighs 1.26 and layer two of the tablets weighs 0.54 gram.

TABLE 4A

Evaluation of Examples 13-20.

| Ex | Resistance to crunch | Friability (%) | Good/Acceptable(Acc)/Poor | Suitable Fast dissolving Chewable tablet | Watering effect 1-5 1 low 5 high |
|---|---|---|---|---|---|
| 13 | 146N | 0.8 | Poor | Too hard Crumble Sandy feeling | 2 |
| 14 | 155N | 1.1 | Poor | Too hard Sandy feeling | 3 |
| 15 | 110N | 1.6 | Acc | Fast dissolving Slightly sandy feeling | 3 |
| 16 | 167N | 0.4 | Poor | Too hard | 4 |
| 17 | 112N | 2.8 | Acc | A loose structure Slightly sandy feeling | 4 |
| 18 | 90N | 2.9 | Acc | A loose structure Quickly dissolve Sandy feeling | 4 |
| 19 | 135N | 0.55 | Poor | Too hard for a chewable table | 4 |
| 20 | 103N | 1.36 | Good | Crunchy nice feeling | 3 |

The above two-layer examples 13-20 were evaluated according to four parameters by a test panel.

Again, two of the parameters were suitability as a chewable tablet and the perceived watering effect. Due to the more complex nature of a two-layer tablet two further parameters were evaluated, namely resistance to crunching and friability.

The resistance to crunching is determined according to European Pharmacopoeia 9.1, test method 2.9.8, by using a pharmaceutical resistance to crunching tester model Pharma Test type PTB 311.

Friability is measured according to European Pharmacopoeia 9.1, test method 2.9.7, by using a pharmaceutical friability-tester PTF 10E from Pharma Test.

When pushed to choose a favorite the test panel pointed to the tablets of examples 18 and 20. The difference between example 18 and examples 20 may among other parameters relate to the different amount of CaCO3. The CaCO3 in the illustrated embodiment tends to give the tablet an attractive loose structure, but too much of it may give a sandy feeling in the mouth.

Both tablets of examples 15 and 17 with lower CaCO3 than example 18 gives acceptable evaluation with only slightly sandy feeling.

Tablets of example 13 and 19 were both found poor in evaluation due to a hard and poor chewability caused by high amount of DC erythritol.

Tablet 14 and 16 were also evaluated poor due to a too hard chewability, this time caused by a too high content of the secondary sugar alcohol being sorbitol, which is known for its excellent binding capabilities

What is claimed is:

1. An oral delivery vehicle tablet, the oral delivery vehicle tablet having been formed by direct compression of a plurality of particles, and the oral delivery vehicle tablet comprising:
   a plurality of non-directly compressible (non-DC) grade erythritol particles in an amount of at least 10% by weight of the oral delivery vehicle tablet;
   a plurality of further sugar alcohol particles; and
   one or more flavoring agents in an amount of 1-10% by weight of the oral delivery vehicle tablet,
   wherein a weight ratio between said plurality of non-DC grade erythritol particles and said plurality of further sugar alcohol particles is between 0.3 and 0.7,
   wherein said plurality of further sugar alcohol particles is different from said plurality of non-DC grade erythritol particles,
   wherein the oral delivery vehicle tablet does not comprise nicotine, and
   wherein said plurality of non-DC grade erythritol particles is particles that have not been subject to granulation steps with said plurality of further sugar alcohol particles, other sugar alcohols, or binders prior to said direct compression.

2. The oral delivery vehicle tablet of claim 1, wherein said plurality of further sugar alcohol particles are directly compressible (DC) grade particles.

3. The oral delivery vehicle tablet of claim 1, wherein said plurality of further sugar alcohol particles comprise sugar alcohols selected from the group consisting of sorbitol, erythritol, xylitol, lactitol, maltitol, mannitol or isomalt or any combination thereof.

4. The oral delivery vehicle tablet of claim 1, wherein friability of the oral delivery vehicle tablet is less than 2%, and wherein friability is measured according to European Pharmacopoeia 9.1, test method 2.9.7. by using a pharmaceutical friability-tester PTF 10E from Pharma Test.

5. The oral delivery vehicle tablet of claim 1, wherein friability of the oral delivery vehicle tablet is greater than 0.2%, and wherein friability is measured according to European Pharmacopoeia 9.1, test method 2.9.7. by using a pharmaceutical friability-tester PTF 10E from Pharma Test.

6. The oral delivery vehicle tablet of claim 1, wherein said plurality of non-DC grade erythritol particles have an average particle size which is larger than the average particle size of said plurality of further sugar alcohol particles, and wherein the average particle size is determined according to the European Pharmacopoeia 9.1 when using test method 2.9.38 particle size distribution estimation by analytical sieving.

7. The oral delivery vehicle tablet of claim 1, wherein a particle size of at least 80% of said plurality of non-DC grade erythritol particles is greater than 200 micron, and wherein the particle size is determined according to European Pharmacopoeia 9.1 when using test method 2.9.38 particle size distribution estimation by analytical sieving.

8. The oral delivery vehicle tablet of claim 1, wherein a particle size of less than 20% of said plurality of non-DC grade erythritol particles is smaller than 250 micron, and wherein the particle size is determined according to European Pharmacopoeia 9.1 when using test method 2.9.38 particle size distribution estimation by analytical sieving.

9. The oral delivery vehicle tablet of claim 1, wherein the oral delivery vehicle tablet comprises at least one module, wherein the module comprises more than 10% by weight of compressed non-DC grade erythritol particles, wherein a resistance to crunching of the module is greater than 60N, and wherein the resistance to crunching is determined according to the European Pharmacopoeia 9.1, test method 2.9.8. by using a pharmaceutical resistance to crunching tester model Pharma Test type PTB 311.

10. The oral delivery vehicle tablet of claim 9, wherein the oral delivery vehicle tablet comprises, in addition to the at least one module, one or more additional modules, wherein each of the at least one module and the one or more additional modules are comprised of compressed particles.

11. The oral delivery vehicle tablet of claim 1, wherein the oral delivery vehicle tablet further comprises 0-60 percent by weight of gum base.

12. The oral delivery vehicle tablet of claim 1, wherein the oral delivery vehicle tablet is free of gum base.

13. The oral delivery vehicle tablet of claim 1, wherein said oral delivery vehicle tablet further comprises a pharmaceutically active ingredient.

14. The oral delivery vehicle tablet of claim 1, wherein said oral delivery vehicle tablet further comprises components for care of mouth and teeth.

15. The oral delivery vehicle tablet of claim 1, wherein said oral delivery vehicle tablet further comprises a mucoadhesive agent.

* * * * *